United States Patent [19]

Aberg et al.

[11] Patent Number: 5,157,025
[45] Date of Patent: Oct. 20, 1992

[54] METHOD FOR LOWERING SERUM CHOLESTEROL EMPLOYING A PHOSPHORUS CONTAINING ACE INHIBITOR ALONE OR IN COMBINATION WITH A CHOLESTEROL LOWERING DRUG

[75] Inventors: A. K. Gunnar Aberg; Mark Kowala, both of Lawrenceville; Patricia Ferrer, Pennington, all of N.J.

[73] Assignee: E. R. Squibb & Sons, Inc., Princeton, N.J.

[21] Appl. No.: 677,921

[22] Filed: Apr. 1, 1991

[51] Int. Cl.$^5$ ............................................. A61K 31/675
[52] U.S. Cl. ..................................... 514/80; 514/89; 514/90; 514/91; 514/94
[58] Field of Search .................. 514/824, 80, 89, 90, 514/91, 94

[56] References Cited

U.S. PATENT DOCUMENTS

| | | | |
|---|---|---|---|
| 4,337,201 | 6/1982 | Petrillo | 548/413 |
| 4,452,790 | 6/1984 | Karanewsky et al. | 424/200 |
| 5,061,694 | 10/1991 | Aberg et al. | 514/19 |

FOREIGN PATENT DOCUMENTS 0219782 11/1982 European Pat. Off. .

OTHER PUBLICATIONS

Roelen, H. C. P. et al., J Med Chem 34(3):1036-1042 1991 (see p. 1037).
Zorn, J. et al., "Prevention of Arteriosclerotic Lesions with Calcium Antagonists of Captopril in Different Rat Hypertension Models," J. Cardiovasc. Pharmacol. vol. 12 (Suppl 6), 1988.
Someya, N. et al., "Suppressive Effect of Captopril on Platelet Aggregation in Essential Hypertension," J. Cardiovasc. Pharmacol. 6:840-843, 1984.
Mizuno, K. et al. "The effects of the angiotensin I-converting enzyme inhibitor, captopril, on serum lipoperoxides level and the renin-angiotensin-aldosterone and Kallikrein-kinin systems in hypertensive patients," Nippon Naibunpi Gakkai Zasshi, Feb. 20, 1984.
Mizuno, K. et al., "Acute effects of captopril on serum lipid peroxides level in hypertensive patients," Tohoku J. Exp. Med., May, 1984, 143(1) 127-8.
Overturf, M. et al., Atherosclerosis, 59:283-299, 1986.
Cecil, Textbook of Medicine, 16 Ed., pp. 239 to 241.
Keilani et al., "Sustained Amelioration of Proteinuria and Lipid Profile Abnormalities in Nephrotic Patients with Renal Impairment Treated with Fosinopril."
Brenner et al., "The Kidney," vol. II, 1981, pp. 1411-1412.
Seldin et al, "The Kidney, Physiology and Pathophysiology," vol. 2, 1985, pp. 1924-1926.

Primary Examiner—Frederick E. Waddell
Assistant Examiner—Diane Gardner
Attorney, Agent, or Firm—Burton Rodney

[57] ABSTRACT

A method is provided for lowering serum cholesterol and thereby inhibiting fatty streak lesions of atherosclerosis by administering to a patient a phosphorus-containing ACE inhibitor, such as fosinopril or ceronapril, alone or in combination with a cholesterol lowering drug, such as pravastatin.

8 Claims, No Drawings

METHOD FOR LOWERING SERUM CHOLESTEROL EMPLOYING A PHOSPHORUS CONTAINING ACE INHIBITOR ALONE OR IN COMBINATION WITH A CHOLESTEROL LOWERING DRUG

FIELD OF THE INVENTION

The present invention relates to a method for lowering serum cholesterol in mammalian species by administering a phosphorus-containing ACE inhibitor, such as fosinopril or ceronapril, alone or in combination with a cholesterol lowering drug, for example an HMG CoA reductase inhibitor, such as pravastatin, lovastatin or simvastatin.

BACKGROUND OF THE INVENTION

It has been shown that captopril, an angiotensin converting enzyme (ACE) inhibitor decreased the development of experimental atherosclerosis in monkeys fed cholesterol (Aberg, G. and Ferrer, P. "Effects of Captopril on Atherosclerosis in Cynomolgus Monkeys," J. Cardiovascular Pharmacology, 15 (suppl.5), S65-S72, 1990), and in the genetic hyperlipidemic Watanabe rabbit (Chobanian, A. V. et al, "Antiatherogenic Effect of Captopril in the Watanabe Heritable Hyperlipidemic Rabbit," Hypertension, 15, 327-331, 1990). It is also known that captopril and cilazapril retarded the proliferation of intimal smooth muscle cells after denuding the carotid artery of rats with a balloom catheter (Powell, J. S. et al, "Inhibitors of Angiotensin-Converting Enzyme Prevent Myointimal Proliferation After Vascular Injury," Science 245, 186-188, 1989). However the effect of ACE inhibitors on the initial cellular events of atherosclerosis remain unkown.

In early atherosclerosis, the monocyte/macrophage is a key player. Hypercholestrolemia promotes the adhesion of blood-borne monocytes to the luminal surface of arteries, and then these leukocytes migrate into the intima. As tissue macrophages, they phagocytose modified LDL particles and transform into foam cells. Foam cells accumulate in the intima to form fatty streaks and they are also present in mature atherosclerotic plaques (Ross, R., "The Pathogenesis of Atherosclerosis—an Update," N. Engl. J. Med., 314, 488-500, 1986; Munro, J. M. and Cotran, R. S., "Biology of Disease. The Pathogenesis of Atherosclerosis: Atherogenesis and Inflammation," Lab. Invest., 58, 249-261, 1988; Steinberg, D. et al, "Beyond Cholesterol. Modifications of Low-Density Lipoprotein that Increases its Atherogenicity," N. Engl. J. Med., 320, 915-924, 1989).

European Patent Application 0219782 to Scholkens (Hoechst) discloses the treatment of atherosclerosis, thrombosis and/or peripheral vascular disease in mammals using an angiotensin converting enzyme (ACE) inhibitor or its physiologically tolerable salts. It further discloses that because ACE is predominantly localized in the luminal plasma membrane of the endothelial cell, ACE inhibitors can interfere in platelet-endothelium interaction. In addition, Scholkens discloses that ACE inhibition potentiates the action of bradykinin (a strong stimulator of prostacyclin release from endothelial cells) by inhibiting its degradation and ACE inhibitors, consequently, have an inhibitory effect on platelet aggregation.

Zorn, J. et al, "Prevention of Arteriosclerotic Lesions with Calcium Antagonists or Captopril in Different Rat Hypertension Models," J. Cardiovasc. Pharmacol. Vol. 12 (Suppl 6), 1988, discloses beneficial effects in mesenteric arteries atherosclerosis with captopril in spontaneous hypertensive Okamoto rats (SHRs), but not in salt-sensitive Dahl rats.

Someya, N. et al, "Suppressive Effect of Captopril on Platelet Aggregation in Essential Hypertension," J. Cardiovasc. Pharmacol. 6:840-843, 1984, discloses at page 840 that "hypertension is closely related to the genesis and progress of atherosclerosis," and that "platelet function plays an important role in atherosclerosis, with platelet dysfunction demonstrable in several vascular diseases. It has been reported that platelet aggregation is increased in hypertensives . . . ." At page 842, it is indicated that the "data demonstrated the inhibition of platelet aggregation in vivo after administration of captopril to hypertensive subjects . . . ." At page 843, it is indicated that "platelet aggregability is greater in hypertensives than in normotensives . . . platelet abnormalities may be a risk factor in atherosclerosis . . . . If captopril possesses an antiplate aggregability effect in addition to its hypotensive effect, it may be very useful for the prevention of atherosclerosis and thrombotic diseases associated with hypertension."

Mizuno, K. et al "The effects of the angiotensin I-converting enzyme inhibitor, captopril, on serum lipoperoxides level and the renin-angiotensinaldosterone and kallikrein-kinin systems in hypertensive patients," Nippon Naibunpi Gakkai Zasshi, Feb. 20, 1984, discloses that captopril is a beneficial antihypertensive agent for preventing serum lipoperoxides concentration (LPX)-induced atherosclerosis in hypertensive patients.

Mizuno, K. et al "Acute effects of captopril on serum lipid peroxides level in hypertensive patients," Tohoku J. Exp. Med., May, 1984, 143(1) p. 127-8, suggests that inhibition of angiotensin-converting enzyme by captopril offers a possible therapeutic approach to the treatment of atherosclerosis complicated with hypertension.

The role of the renin-angiotensin system in atherosclerosis is not clear. Campbell-Boswell Robertson, Exp. and Mol. Pathol. 35:265 (1981) reported that angiotensin II stimulated proliferation of isolated human vascular smooth muscle cells while Geisterfer et al, Circ. Res. 62: 749-756 (1988) showed no proliferation (but stimulation of growth) of isolated rat vascular smooth muscle cells.

Overturf, M. et al, Atherosclerosis, 59:383-399, 1986, discloses that studies with ACE inhibitors in cholesterol fed rabbits show no significant effects in the development of atherosclerosis.

Cecil, Textbook of Medicine, 16 Ed., pp 239 to 241, indicates at page 240 that blood pressure is an accelerator of atherosclerosis.

U.S. Pat. Nos. 4,046,889 and 4,105,776 to Ondetti et al disclose proline derivatives, including captopril, which are angiotensin converting enzyme (ACE) inhibitors useful for treating hypertension.

U.S. Pat. No. 4,337,201 to Petrillo discloses phosphinylalkanoyl substituted prolines, including fosinopril, which are ACE inhibitors useful for treating hypertension.

U.S. Pat. No. 4,374,829 discloses carboxyalkyl dipeptide derivatives, including enalapril, which are ACE inhibitors useful for treating hypertension.

U.S. Pat. No. 4,452,790 to Karanewsky et al discloses phosphonate substituted amino or imino acids and salts thereof and covers (S)-1-[6-amino-2-[[hydroxy(4-phenylbutyl)phosphinyl]oxy-1-oxohexyl]-L-proline (SQ 29,852, ceronapril). These compounds are ACE inhibitors useful in treating hypertension.

DESCRIPTION OF THE INVENTION

In accordance with the present invention, a method is provided for lowering serum cholesterol, in mammalian species, wherein a therapeutically effective amount of a phosphorus-containing angiotensin converting enzyme (ACE) inhibitor, such as fosinopril, alone or in combination with a cholesterol lowering drug, is administered systemically, such as orally or patenterally.

It has been found that the phosphorus-containing ACE inhibitor lowers serum cholesterol by reducing plasma very low density lipoproteins (VLDL) and low density lipoproteins (LDL) as well as reducing plasma triglycerides, and increases high density lipoprotein cholesterol.

In addition, in accordance with the present invention, a method is provided for inhibiting or preventing atherosclerosis by reducing plasma cholesterol and thereby inhibiting fatty streak lesions of atherosclerosis, in mammalian species, wherein a therapeutically effective amount of a phosphorus-containing ACE inhibitor alone or in combination with a cholesterol lowering drug, is administered systemically, such as orally or parenterally.

The phosphorus-containing ACE inhibitor may be administered to hypertensive patients or normotensive patients in accordance with the method of the present invention.

Where the patient to be treated in accordance with the present invention is normotensive, the phosphorus angiotensin converting enzyme inhibitor may be administered in amounts below that required to cause hemodynamic effects, that is below that required to cause a reduction in blood pressure. Where the patient to be treated is hypertensive, then the phosphorus-containing angiotensin converting enzyme inhibitor will be used in amounts usually employed to treat hypertension.

The combination of the phosphorus-containing ACE inhibitor and cholesterol lowering drug will be employed in a weight ratio to each other of within the range of from about 1000:1 to about 0.001 and preferably from about 0.05:1 to about 100:1.

The phosphorus-containing ACE inhibitors suitable for use herein include the phosphinylalkanoyl substituted prolines disclosed in U.S. Pat. No. 4,337,201 mentioned above with fosinopril being preferred, phosphonate substituted amino or imino acids or salts disclosed in U.S. Pat. No. 4,452,790 with (s)-1-[6-amino-2-[[hydroxy-(4-phenylbutyl)phosphinyl]oxy]-1-oxohexyl]-L-proline (SQ 29,852 or ceronapril) being preferred, the phosphinylalkanoyl prolines disclosed in U.S. Pat. No. 4,168,267 and the phosphonamidates disclosed in U.S. Pat. No. 4,432,971.

The phosphinylalkanoyl substituted prolines disclosed in U.S. Pat. No. 4,337,201 to Petrillo have the formula

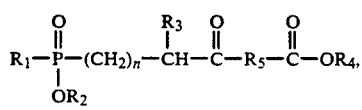

or a salt thereof, wherein $R_1$ is alkyl, aryl, arylalkyl, cycloalkyl or cycloalkylalkyl;

one of $R_2$ and $R_4$ is

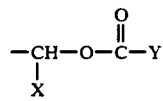

and the other is hydrogen, alkyl, aryalkyl or

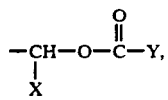

wherein X is hydrogen, alkyl or phenyl and Y is hydrogen, alkyl, phenyl or alkoxy, or together X and Y are —(CH$_2$)$_2$—, —(CH$_2$)$_3$—, —CH=CH— or

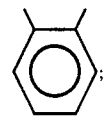

$R_3$ is hydrogen or alkyl;

—$R_5$—COOR$_4$ is

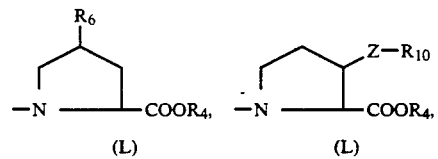

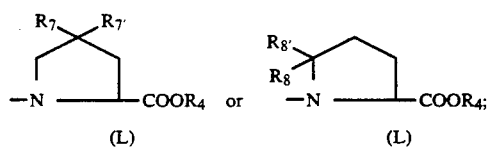

$R_6$ is hydrogen, hydroxy, alkyl, halogen, azido, amino, cycloalkyl, aryl, arylalkyl, carbamoyloxy, N,N-dialkylcarbamoyloxy, or —Z—$R_9$;

$R_7$ and $R'_7$ are the same and each is halogen or —Z—$R_{10}$, $R_7$ and $R'_7$ together are =O, —O—(CH$_2$)$_m$—O— or —S—(CH$_2$)$_m$—S—;

$R_8$ is hydrogen and $R'_8$ is phenyl, 2-hydroxyphenyl or 4-hydroxyphenyl or $R_8$ and $R'_8$ together are =O;

$R_9$ is alkyl, aryl, arylalkyl, 1- or 2-naphthyl, or biphenyl;

$R_{10}$ is alkyl, aryl or arylalkyl;

Z is oxygen or sulfur;

n is 0 or 1; and m is 1 or 2.

The Petrillo patent covers fosinopril

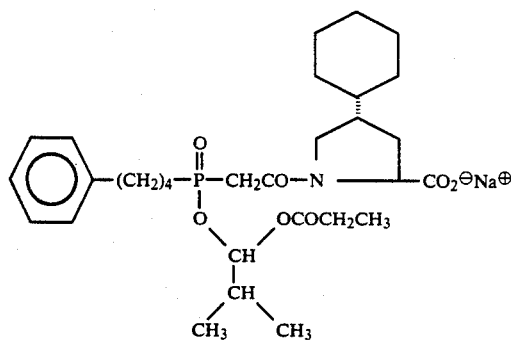

which is most preferred.

The phosphonamidate substituted amino or imino acids disclosed in U.S. Pat. No. 4,432,971 to Karanewsky et al have the formula

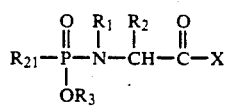

wherein X is an imino or amino acid of the formula

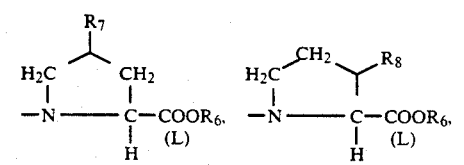

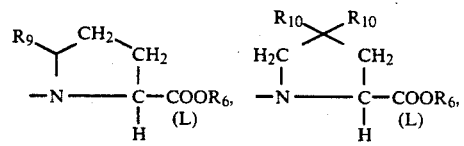

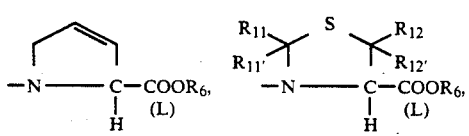

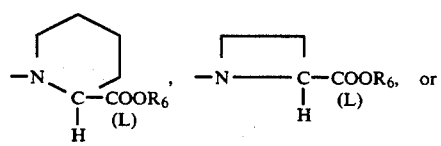

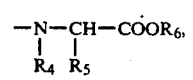

$R_7$ is hydrogen, lower alkyl, halogen, keto, hydroxy,

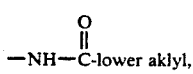

azido, amino,

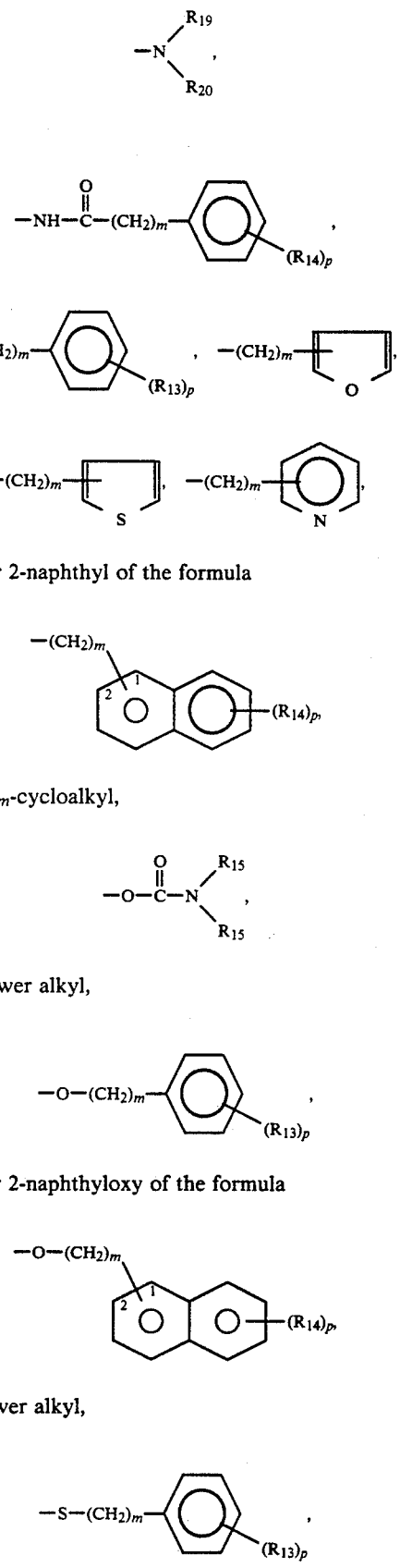

a 1- or 2-naphthyl of the formula

—$(CH_2)_m$-cycloalkyl,

—O—lower alkyl, a 1- or 2-naphthyloxy of the formula

—S—lower alkyl, or a 1- or 2-naphthylthio of the formula

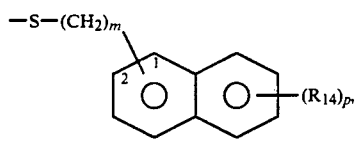

$R_8$ is keto, halogen,

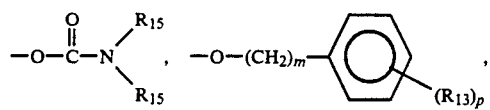

—O—lower alkyl, a 1- or 2-naphthyloxy of the formula

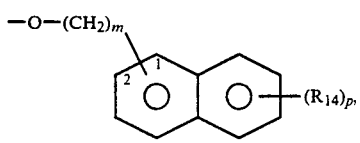

—S—lower alkyl,

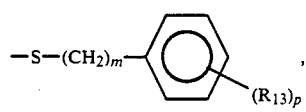

or a 1- or 2-naphthylthio of the formula

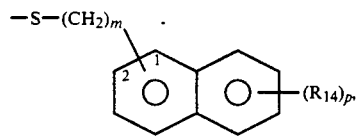

$R_9$ is keto or

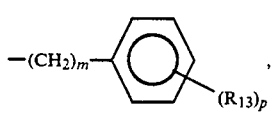

$R_{10}$ is halogen or —Y—$R_{16}$, $R_{11}$, $R'_{11}$, $R_{12}$ and $R'_{12}$ are independently selected from hydrogen and lower alkyl or $R'_{11}$, $R_{12}$ and $R'_{12}$ are hydrogen and $R_{11}$ is

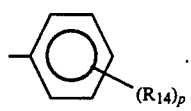

$R_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

$R_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl or hydroxy.

m is zero, one, two or three.

p is one, two or three provided that p is more than one only if $R_{13}$ or $R_{14}$ is hydrogen, methyl, methoxy, chloro or fluoro.

$R_{15}$ is hydrogen or lower alkyl of 1 to 4 carbons.

Y is oxygen or sulfur.

$R_{16}$ is lower alkyl of 1 to 4 carbons,

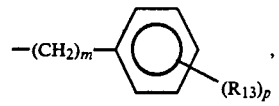

or the $R_{16}$ groups join to complete an unsubstituted 5- or 6-membered ring or said ring in which one or more of the carbons has a lower alkyl of 1 to 4 carbons or a di(lower alkyl of 1 to 4 carbons) substituent.

$R_4$ is hydrogen, lower alkyl, cycloalkyl, or

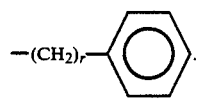

$R_5$ is hydrogen, lower alkyl,

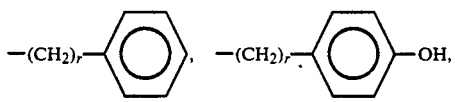

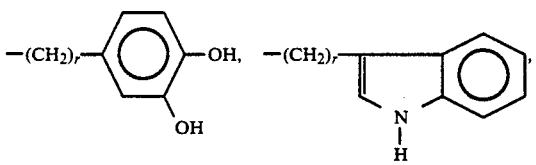

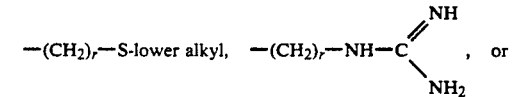

r is an integer from 1 to 4, $R_1$ is hydrogen, lower alkyl or cycloalkyl.

$R_2$ is hydrogen, lower alkyl, halo substituted lower alkyl,

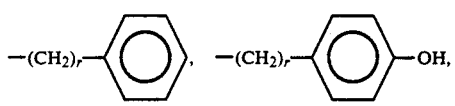

-continued

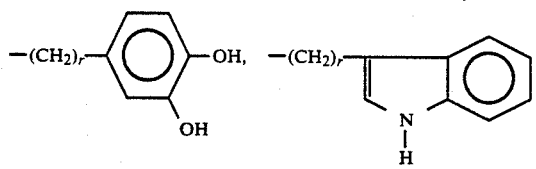

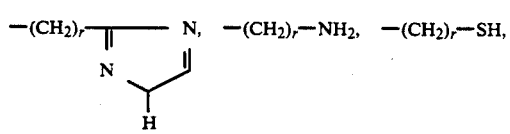

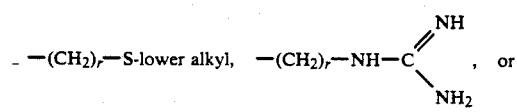

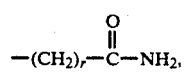

or $R_1$ and $R_2$ taken together are —$(CH_2)_n$— wherein n is an integer from 2 or 4.

$R_3$ and $R_6$ are independently selected from hydrogen, lower alkyl, benzyl, benzhydryl, or

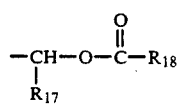

wherein $R_{17}$ is hydrogen, lower alkyl, or phenyl, and $R_{18}$ is hydrogen, lower alkyl, lower alkoxy, phenyl, or $R_{17}$ and $R_{18}$ taken together are —$(CH_2)_2$—, —$(CH_2)_3$—, —$CH=CH$—, or

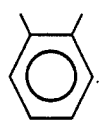

$R_{19}$ is lower alkyl, benzyl, or phenethyl.
$R_{20}$ is hydrogen, lower alkyl, benzyl or phenethyl.
$R_{21}$ is alkyl of 1 to 10 carbons,

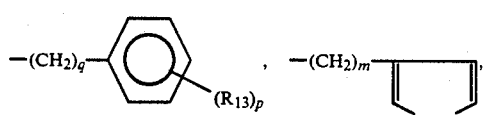

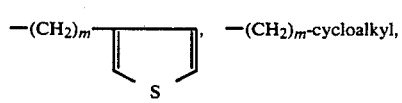

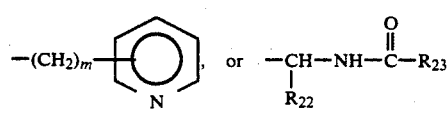

wherein q is zero or an integer from 1 to 7 and $R_{14}$, p and m are as defined above.

$R_{22}$ and $R_{23}$ are independently selected from hydrogen, lower alkyl, halo substituted lower alkyl,

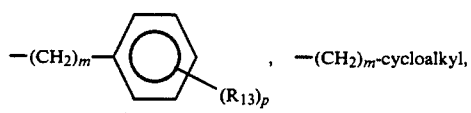

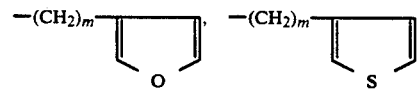

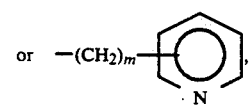

wherein m, $R_{14}$, and p are as defined above.

The phosphonate substituted amino or imino acids or salts disclosed in U.S. Pat. No. 4,452,790 to Karanewsky et al have the formula

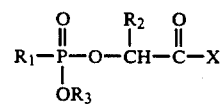

wherein X is an imino or amino acid of the formula

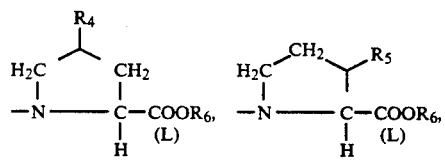

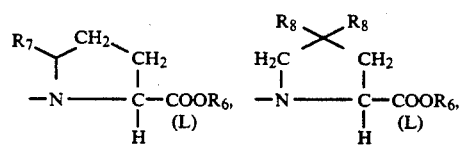

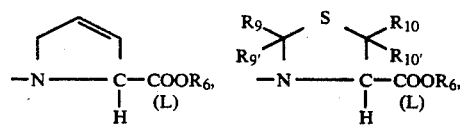

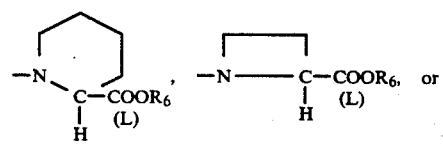

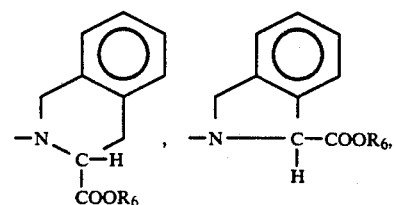

-continued

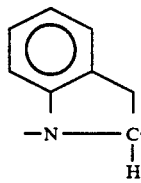
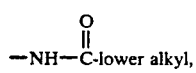

$R_4$ is hydrogen, lower alkyl, halogen, keto, hydroxy,

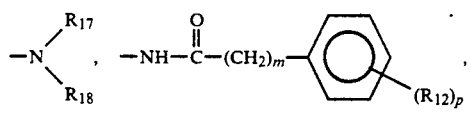

azido, amino,

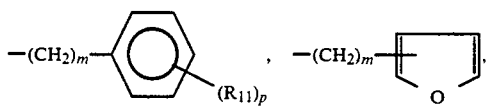

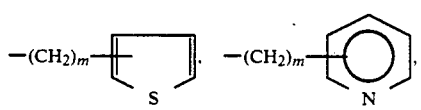

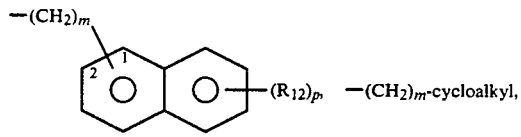

a 1- or 2-naphthyl of the formula

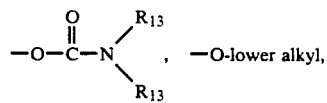

a 1- or 2-naphthyloxy of the formula

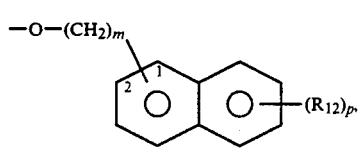

—S—lower alkyl,

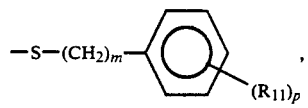

or a 1- or 2-naphthylthio of the formula

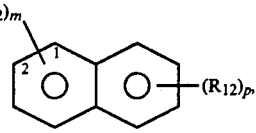

$R_5$ is keto, halogen,

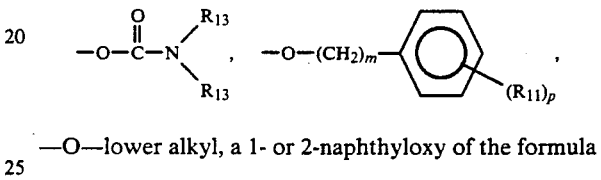

—O—lower alkyl, a 1- or 2-naphthyloxy of the formula

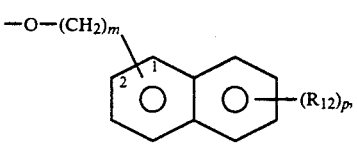

—S—lower alkyl,

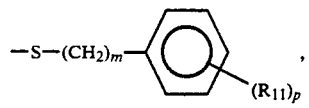

or a 1- or 2-naphthylthio of the formula

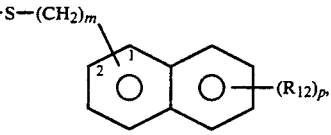

$R_7$ is keto or

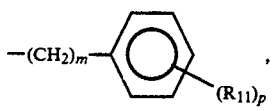

Each $R_8$ is independently halogen or —Y—$R_{14}$.
$R_9$, $R_9{'}$, $R_{12}$ and $R_{10}{'}$ are independently selected from hydrogen and lower alkyl or $R_9{'}$, $R_{10}$ and $R_{10}{'}$ are hydrogen and $R_9$ is

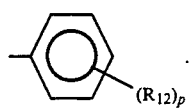

$R_{11}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

$R_{12}$ is hydrogen, lower alkyl of 1 to 4 carbons, lower alkoxy of 1 to 4 carbons, lower alkylthio of 1 to 4 carbons, chloro, bromo, fluoro, trifluoromethyl or hydroxy.

m is zero, one, two or three.

p is one, two or three provided that p is more than one only if $R_{11}$ or $R_{12}$ is hydrogen, methyl, methoxy, chloro or fluoro.

$R_{13}$ is hydrogen or lower alkyl of 1 to 4 carbons.

Y is oxygen or sulfur.

$R_{14}$ is lower alkyl of 1 to 4 carbons,

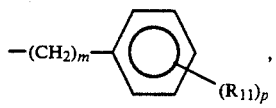

or the $R_{14}$ groups join to complete an unsubstituted 5- or 6-membered ring or said ring in which one or more of the carbons has a lower alkyl of 1 to 4 carbons or a di(lower alkyl of 1 to 4 carbons) substituent.

$R_{21}$ is hydrogen, lower alkyl, cycloalkyl, phenyl or

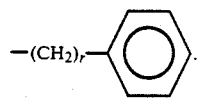

$R_{22}$ is hydrogen, lower alkyl,

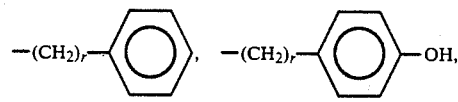

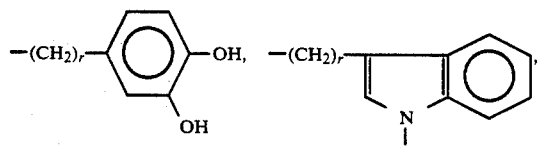

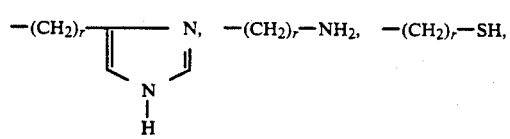

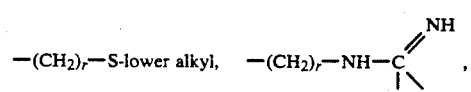

or 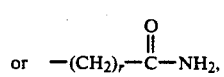

r is an integer from 1 to 4.

$R_1$ is alkyl of 1 to 10 carbons, aminoalkyl, haloalkyl,

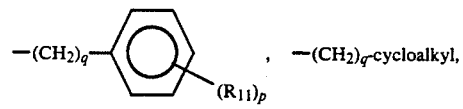

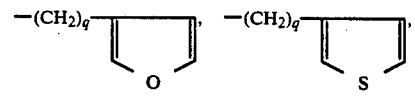

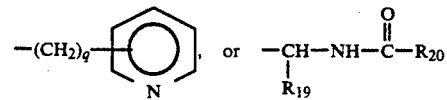

wherein q is zero or an integer from 1 to 7 and $R_{12}$ and p are as defined above.

$R_{19}$ and $R_{20}$ are independently selected from hydrogen, lower alkyl, halo substituted lower alkyl,

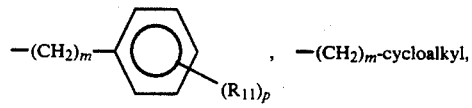

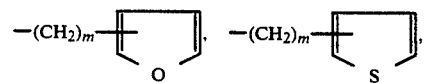

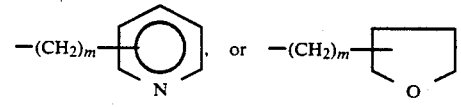

wherein m, $R_{11}$, and p are as defined above.

$R_2$ is hydrogen, lower alkyl, halo substituted lower alkyl,

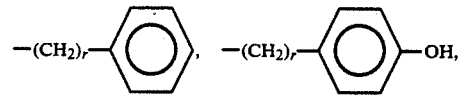

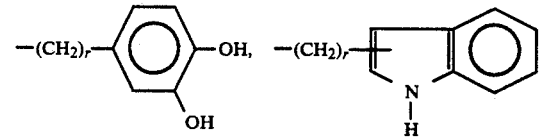

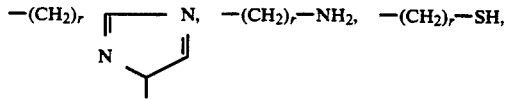

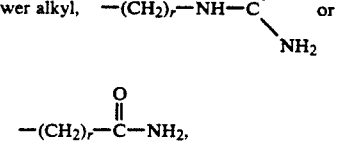

wherein r is as defined above.

$R_3$ and $R_6$ are independently selected from hydrogen, lower alkyl, benzyl, alkali metal such as Li, Na or K, benzhydryl,

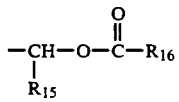

wherein $R_{15}$ is hydrogen, lower alkyl, cycloalkyl or phenyl, and $R_{16}$ is hydrogen, lower alkyl, lower alkoxy, phenyl, or $R_{15}$ and $R_{16}$ taken together are $-(CH_2)_2-$, $-(CH_2)_3-$, $-CH=CH-$, or

$R_{17}$ is lower alkyl, benzyl, or phenethyl.

$R_{18}$ is hydrogen, lower alkyl, benzyl or phenethyl. Preferred is (S)-1-[6-amino-2-[[hydroxy-(4-phenyl-butyl)phosphinyl]oxy]-1-oxohexyl]-L-proline

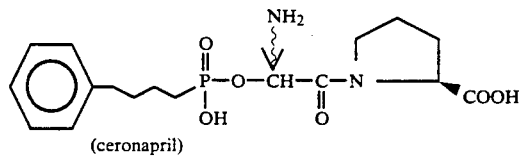

(ceronapril)

The phosphinylalkanoyl prolines disclosed in U.S. Pat. No. 4,168,267 to Petrillo have the formula

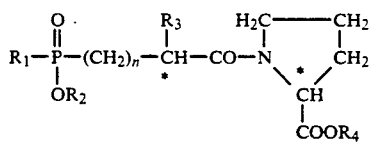

wherein
$R_1$ is lower alkyl, phenyl or phenyl-lower alkyl;
$R_2$ is hydrogen, phenyl-lower alkyl or a metal ion;
$R_3$ is hydrogen or lower alkyl;
$R_4$ is hydrogen, lower alkyl, phenyl-lower alkyl or a metal ion; and
n is 0 or 1.

Cholesterol lowering drugs or drugs which are inhibitors of cholesterol biosynthesis which may be used in the method of the invention include HMG CoA reductase inhibitors, squalene synthetase inhibitors, fibric acid derivatives, bile acid sequestrants, probucol, niacin, niacin derivatives and the like.

The HMG CoA reductase inhibitors suitable for use herein include, but are not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, velostatin (synvinolin) and related compounds as disclosed in U.S. Pat. Nos. 4,448,784 and 4,450,171, with lovastatin, pravastatin or velostatin being preferred. Other HMG CoA reductase inhibitors which may be employed herein include, but are not limited to, fluindostatin (Sandoz XU-62-320), pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)alkyl]pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propanephosphonic acid derivatives as disclosed in French Patent No. 2,596,393, 2,3-di-substituted pyrrole, furan and thiophene derivatives as disclosed in European Patent Application No. 0221025, naphthyl analogs of mevalonolactone as disclosed in U.S. Pat. No. 4,686,237, octahydro-naphthalenes such as disclosed in U.S. Pat. No. 4,499,289, keto analogs of mevinolin (lovastatin) as disclosed in European Patent Application No. 0,142,146 A2, BMS-180542 [4R-[4α,6β(E)]-6-[4,4-bis(4-fluorophenyl)-3-(1-methyl-1H-tetrazol-5-yl)-1,3-butadienyl]tetrahydro-4-hydroxy-2H-pyran-2-one disclosed in U.S. Pat. No. 4,897,490, as well as other known HMG CoA reductase inhibitors.

In addition, phosphinic acid compounds useful in inhibiting HMG CoA reductase suitable for use herein are disclosed in GB 2205837 which compounds have the moiety

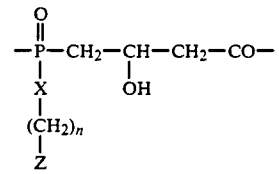

wherein X is $-O-$ or $-NH-$, n is 1 or 2 and Z is a hydrophobic anchor.

Examples of such compounds include
(S)-4-[[[4'-fluoro-3,3',5-trimethyl[1,1'-bipheny]-methoxy]methoxyphosphinyl]-3-hydroxy-butanoic acid, methyl ester or its monolithium salt,
(S)-4-[[[4'-fluoro-3,3',5-trimethyl[1,1'-biphenyl]-2-yl]methoxy]hydroxyphosphinyl]-3-hydroxybutanoic acid, dilithium salt,
(3S)-4-[[[4'-fluoro-3,3',5-trimethyl[1,1'-biphenyl-2-yl]methoxy]methylphosphinyl]-3-hydroxybutanoic acid, monolithium salt,
(S)-4-[[[2,4-dichloro-6-[(4-fluorophenyl)-methoxy]-phenyl]methoxy]methoxyphosphinyl]-3-hydroxybutanoic acid, monolithium salt,
(3S)-4-[[[2,4-dichloro-6-[(4-fluorophenyl)-methoxy]-phenylmethoxy]hydroxyphosphinyl]-3-hydroxybutanoic acid, dilithium salt,
(3S)-4-[2,4-dichloro-6-[(4-fluorophenyl)-methoxy]-phenyl]methoxy]methylphosphinyl]-3-hydroxybutanoic acid, or its methyl ester, and
(S)-4-[[[4'-fluoro-3,3',5-trimethyl[1,1'-biphenyl-2-yl]methylamino]methoxyphosphinyl]-3-hydroxybutanoic acid, monolithium salt.

Another class of HMG CoA reductase inhibitors suitable for use herein include phosphinic acid compounds disclosed in GB 2205838, which compounds have the moiety

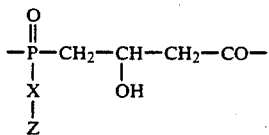

wherein X is —CH₂— —CH₂—CH₂—, —CH=CH—, —CH₂CH₂CH₂—, —C≡C— or —CH₂O—, where O is linked to Z, and Z is a hydrophobic anchor.

Examples of such compounds include (S)-4-[[[1-(4-fluorophenyl)-3-(1-methylethyl)-1H-indol-2-yl]ethynyl]hydroxyphosphinyl]-3-hydroxyfutanoic acid, or its sodium salt (SQ 33,600) (preferred) or its dilithium salt;
(S)-4-[[(E)-2-[4'-fluoro-3,3',5-trimethyl-[1,1'-biphenyl]-2-yl]ethenyl]hydroxyphosphinyl]-3-hydroxybutanoic acid or its dilithium salt;
(S)-4-[2-[4'-fluoro-3,3',5-trimethyl-[1,1'-biphenyl]-2-yl]ethyl]hydroxyphosphinyl]-3-hydroxybutanoic acid, methyl ester or mono- or di-alkali metal salts thereof;
(S)-4-[[[4'-fluoro-3,3',5-trimethyl-[1,1'-biphenyl]-2-yl]ethynyl]methoxyphosphinyl]-3-hydroxybutanoic acid or the methyl ester thereof;
(5Z)-4-[[2-4'-fluoro-3,3',5-trimethyl-[1,1'-biphenyl]-2-yl]ethenyl]hydroxyphosphinyl]-3-hydroxybutanoic acid, methyl esters thereof;
(S)-4-[[2-[3-(4-fluorophenyl)-1-(1-methyl-ethyl)-1H-indol-2-yl]ethyl]methoxyphosphinyl]3-hydroxybutanoic acid, methyl esters;
(S)-4-[[2-[[1,1'-biphenyl]-2-yl]ethyl]-methoxyphosphinyl-3-hydroxybutanoic acid, methyl ester;
(S)-4-[[2-[4'-fluoro-3,3',5-trimethyl-[1,1'-biphenyl-2-yl]ethyl]hydroxyphosphinyl]3-hydroxybutanoic acid, dilithium salt;
(S)-4-[[2-[4'-fluoro-3,3',5-trimethyl-1,1'-biphenyl]-2-yl]ethynyl]hydroxyphosphinyl]-3-hydroxybutanoic acid, dilithium salt;
(SZ)-4-[[2-[4'-fluoro-3,3',5-trimethyl-[1,1'-biphenyl]-2-ylethenyl]hydroxyphosphinyl]-3-hydroxybutanoic acid, dilithium salt;
(S)-4-[[2-[3-(4-fluorophenyl)-1-(1-methyl-ethyl)-1H-indol-2-yl]ethyl]hydroxyphosphinyl-3-hydroxybutanoic acid, dilithium salt;
(S)-4-[[2-[(1,1'-biphenyl-2-yl]ethyl]-hydroxyphosphinyl]-3-butanoic acid, dilithium salt;
(S)-4-(hydroxymethoxyphosphinyl)-3-[[(1,1-dimethylethyl)diphenylsilyloxybutanoic acid, methyl ester, or its dicyclohexylamine (1:1) salt;
(E)-4-[[2-[3-(4-fluorophenyl)-1-(1-methyl-ethyl)-1H-indol-2-yl]ethenyl]hydroxyphosphinyl]-3-hydroxybutanoic acid or its dilithium salt or methyl ester thereof;
4-[[2-[4'-fluoro-3,3',5-trimethyl[1,1'-biphenyl-2-yl]ethyl]hydroxyphosphinyl]-3-hydroxybutanoic acid or its dilithium salt or methyl ester thereof;
(E)-4-[[2-[4'-fluoro-3,3',5-trimethyl[1,1'-biphenyl]-2-yl]ethenyl]hydroxyphosphinyl]-3-hydroxybutanoic acid or its dilithium salt or methyl ester thereof;
(S)-4-[[2,4-dimethyl-6-[(4-fluorophenyl)-methoxy]-phenyl]ethyl]hydroxyphosphinyl]-3-hydroxybutanoic acid or its dilithium salt or methyl ester thereof;
(S)-4-[[[2,4-dimethyl-6-[(4-fluorophenyl)-methoxy]-phenylethynyl]hydroxyphosphinyl]-3-hydroxybutanoic acid or its dilithium salt or methyl ester thereof;
(S)-4-[[2-[3,5-dimethyl[1,1'-biphenyl)-2-yl]ethyl]hydroxyphosphinyl]-3-hydroxybutanoic acid or its dilithium salt or methyl ester thereof;
(S)-4-[[2-[4'-fluoro-3,5-dimethyl[1,1'-biphenyl]-2-ylethyl]hydroxyphosphinyl]-3-hydroxybutanoic acid or its dilithium salt or methyl ester thereof;
(S)-4-[2-[[1,1'-biphenyl]-2-yl]ethynyl]-hydroxyphosphinyl]-3-hydroxybutanoic acid or its dilithium salt or methyl ester thereof;
(S)-4-[[2-(5-(4-fluorophenyl)-3-(1-methylethyl)-1-phenyl-1H-pyrazol-4-yl]ethynyl]methoxyphosphinyl]-3-hydroxybutanoic acid, methyl ester;
(S)-4-[[2-1-(4-fluorophenyl)-3-(1-methylethyl)-1-indol-2-yl]ethynyl]hydroxyphosphinyl]-3-hydroxybutanoic acid or its dilithium salt or disodium salt or methyl ester thereof;
(S)-4-[[2-[1-(4-fluorophenyl)-3-(1-methylethyl)-1H-indol-2-yl]ethyl]hydroxyphosphinyl]-3-hydroxybutanoic acid or its dilithium salt or methyl ester thereof;
(S)-4-[[2-[5-(4-fluorophenyl)-3-(1-methylethyl)-1-phenyl-1H-pyrazol-4-yl]ethynyl]hydroxyphosphinyl]-3-hydroxybutanoic acid, dilithium salt;
(E)-4-[[2-[5-(4-fluorophenyl)-3-(1-methylethyl)-1-phenyl-1H-pyrazol-4-yl]ethenyl]methoxyphosphinyl]-3-hydroxybutanoic acid, methyl ester;
(E)-4-[2-5-(4-fluorophenyl)-3-(1-methylethyl)-1-phenyl-1H-pyrazol-4-yl]ethenylhydroxyphosphinyl]-3-hydroxybutanoic acid, dilithium salt;
(S)-4-[[2-[5-(4-fluorophenyl)-3-(1-methylethyl)-1-phenyl-1H-pyrazol-4-ylethyl]methoxyphosphinyl]-3-hydroxybutanoic acid, methyl ester;
(S)-4-[[2-[5-(4-fluorophenyl)-3-(1-methylethyl)-1-phenyl-1H-pyrazol-4-ylethyl]hydroxyphosphinyl]-3-hydroxybutanoic acid, dilithium salt;
(S)-4-[2-[3-(4-fluorophenyl)-5-(1-methylethyl)-1-phenyl-1H-pyrazol-4-yl]ethyl]methoxyphosphinyl]-3-hydroxybutanoic acid, methyl ester;
(S)-4-[[2-3-(4-fluorophenyl)-5-(1-methylethyl)-1-phenyl-1H-pyrazol-4-yl]ethyl]hydroxyphosphinyl]-3-hydroxybutanoic acid, dilithium salt;
(S)-4-[[2-[3-(4-fluorophenyl)-5-(1-methylethyl)-1-phenyl-1H-pyrazol-4-yl]ethynylmethoxyphosphinyl]-3-hydroxybutanoic acid, methyl ester;
(S)-4-[2-[3-(4-fluorophenyl)-5-(1-methylethyl)-1-phenyl-1H-pyrazol-4-yl]ethynyl]hydroxyphosphinyl]-3-hydroxybutanoic acid, dilithium salt;
(S)-4-[[4-(4-fluorophenyl)-1-(1-methylethyl)-3-phenyl-1H-pyrazol-5-yl]ethynyl]methoxyphosphinyl]-3-hydroxybutanoic acid, methyl ester;
(S)-4-[[[4-(4-fluorophenyl)-1-(1-methylethyl)-3-phenyl-1H-pyrazol-5-yl]ethynyl]hydroxyphosphinyl]-3-hydroxybutanoic acid, dilithium salt;
(S)-4-[[2-[4-(4-fluorophenyl)-1-(1-methylethyl)-3-phenyl-1H-pyrazol-5-yl]ethyl]methoxyphosphinyl]-3-hydroxybutanoic acid, methyl ester;
(S)-4-[[2-[4-(4-fluorophenyl)-1-(1-methylethyl)-3-phenyl-1H-pyrazol-5-yl]ethyl]hydroxyphosphinyl]-3-hydroxybutanoic acid, dilithium salt;
(S)-4-[[[1-(4-fluorophenyl)-4-(1-methylethyl)-2-phenyl-1H-imidazole-5-ylethynyl]methoxyphosphinyl]-3-hydroxybutanoic acid, methyl ester;
(S)-4-[[1-(4-fluorophenyl)-4-(1-methylethyl)-2-phenyl-1H-imidazole-5-yl]ethynyl]methoxyphosphinyl]-3-hydroxybutanoic acid, methyl ester;

(S)-4-[[2-[1-(4-fluorophenyl)-4-(1-methylethyl)-2-phenyl-1H-imidazol-5-yl]ethyl]methoxyphosphinyl]-3-hydroxybutanoic acid, methyl ester;

(S)-4-[[2-[1-(4-fluorophenyl)-4-(1-methylethyl)-2-phenyl-1H-imidazol-5-yl]ethyl]hydroxyphosphinyl]-3-hydroxybutanoic acid, dilithium salt;

(S)-4-[[[2-(cyclohexylmethyl)-4,6-dimethylphenyl]ethynylhydroxyphosphinyl]-3-hydroxybutanoic acid or its dilithium salt or methyl ester thereof;

4-[[2-[2-(cyclohexylmethyl)-4,6-dimethylphenyl]ethenyl]hydroxyphosphinyl]-3-hydroxybutanoic acid or its dilithium salt or methyl ester thereof;

(S)-4-[[2-[2-(cyclohexylmethyl)-4,6-dimethylphenyl]ethyl]hydroxyphosphinyl]-3-hydroxybutanoic acid or its dilithium salt or methyl ester thereof;

4-[[[[4'-fluoro-3,3',5-trimethyl[1,1'-biphenyl-2-yl]oxy]methyl]hydroxyphosphinyl]-3-hydroxybutanoic acid or its dilithium salt or methyl ester thereof;

4-[[[4'-fluoro-3,3',5-trimethyl[1,1'-biphenyl]-2-yl]methyl]hydroxyphosphinyl]-3-hydroxybutanoic acid or its dilithium salt or methyl ester thereof;

(S)-4-[[[1-(4-fluorophenyl)-3-methyl-2-naphthalenyl]ethynyl]hydroxyphosphinyl]-3-hydroxybutanoic acid or its dilithium salt or methyl ester thereof;

(E)-4-[2-[1-(4-fluorophenyl)-3-methyl-2-naphthalenyl]ethenyl]hydroxyphosphinyl]-3-hydroxybutanoic acid or its dilithium salt or methyl ester thereof;

(S)-4-[[2-[1-(4-fluorophenyl)-3-methyl-2-naphthalenyl]ethyl]hydroxyphosphinyl]-3-hydroxybutanoic acid or its dilithium salt or methyl ester thereof;

4-[[3-[4'-fluoro-3,3',5-trimethyl[1,1'-biphenyl-2-yl]propyl]methoxyphosphinyl]-3-hydroxybutanoic acid, methyl ester;

4-[3-[4'-fluoro-3,3',5-trimethyl[1,1'-biphenyl]-2-yl]propyl]hydroxyphosphinyl]-3-hydroxybutanoic acid, dilithium salt;

[1S-[1α(R*),2α,4αβ,8β,8αα]]-4-[[2-[8-(2,2-dimethyl-1-oxobutoxy)decahydro-2-methyl-1-naphthalenyl]ethyl]methoxyphosphinyl]-3-hydroxybutanoic acid, methyl ester;

[1S-[1α(R*),2α,4αβ,8β,8αβ]]-4-[[2-[8-(2,2-dimethyl-1-oxobutoxy)decahydro-2-methyl-1-naphthalenyl]ethyl]hydroxyphosphinyl]-3-hydroxybutanoic acid, dilithium salt;

(S)-4-[[[3'-(4-fluorophenyl)spiro]cyclopentane-1,1'-[1H]indene]-2-yl]ethynyl]methoxyphosphinyl]-3-hydroxybutanoic acid, methyl ester; and (S)-4-[[[3'-(4-fluorophenyl)spiro]cyclopentane-1,1'-[1H]indene-2-yl]ethynyl]hydroxyphosphinyl]-3-hydroxybutanoic acid, dilithium salt.

The squalene synthetase inhibitors suitable for use herein include, but are not limited to, those disclosed by Biller et al, J. Med. Chem. 1988, Vol. 31, No. 10, pp 1869-1871, including isoprenoid (phosphinylmethyl)-phosphonates such as those of the formula

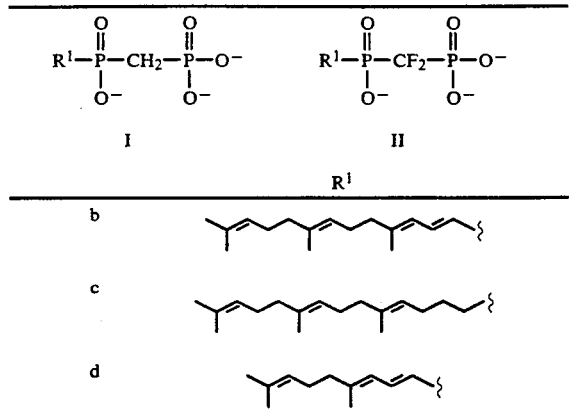

including the triacids thereof, triesters thereof and tripotassium and trisodium salts thereof as well as other squalene synthetase inhibitors disclosed in pending U.S. Pat. Nos. 4,871,721 and 4,924,024 and in Biller et al, J. Med. Chem. 1988, Vol. 31, No. 10, pp 1869 to 1871.

In addition, other squalene synthetase inhibitors suitable for use herein include the terpenoid pyrophosphates disclosed by P. Ortiz de Montellano et al., J. Med. Chem.; 1977, 20, 243-249, the farnesyl diphosphate analog A and presqualene pyrophosphate (PSQ-PP) analogs as disclosed by Corey and Volante, J. Am. Chem. Soc. 1976, 98, 1291–1293, phosphinylphosphonates reported by McClard, R. W. et al., J.A.C.S., 1987, 109, 5544 and cyclopropanes reported by Capson, T. L., PhD dissertation, June, 1987, Dept. Med. Chem. U. of Utah, Abstract, Table of Contents, pp. 16, 17, 40–43, 48–51, Summary.

Preferred are pravastatin, lovastatin or velostatin or a squalene synthetase inhibitor such as disclosed by Biller et al., supra or combinations thereof which include a weight ratio of the HMG CoA reductase inhibitor:squalene synthetase inhibitor of from about 0.05:1 to about 100:1.

Other cholesterol lowering drugs which function other than by inhibiting the enzyme HMG CoA reductase or squalene synthetase suitable for use herein include, but are not limited to, antihyperlipoproteinemic agents such as fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex ®, Polidexide ®), as well as clofibrate, lipostabil (Rhone-Poulenc), Eisai E-5050 (an N-substituted ethanolamine derivative), imanixil (HOE-402) tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents which lower cholesterol through a mechanism other than by the inhibition

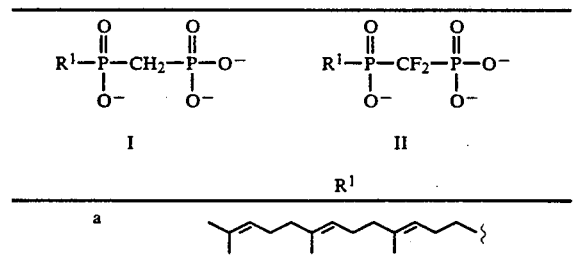

of the enzyme HMG CoA reductase or squalene synthetase.

Also preferred are combinations of any of the HMG CoA reductase inhibitors, preferably pravastatin, or isoprenoid (phosphinylmethyl) phosphonates disclosed by Biller et al., supra, gemfibrozil or fenofibrate.

Preferred are those ACE inhibitors which are substituted proline derivatives and most preferred is fosinopril.

The above-mentioned U.S. patents are incorporated herein by reference.

In carrying out the method of the present invention, the phosphorus-containing ACE inhibitor alone or in combination with the cholesterol lowering drug may be administered to mammalian species, such as monkeys, dogs, cats, rats, humans, etc., and as such may be incorporated in a conventional systemic dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfite) or the like. Oral dosage forms are preferred, although parenteral forms are quite satisfactory as well.

The dose administered must be carefully adjusted according to age, weight and condition of the patient, as well as the route of administration, dosage form and regimen and the desired result.

For oral administration, a satisfactory result may be obtained employing the phosphorus-containing ACE inhibitor in an amount within the range of from about 0.01 mg/kg to about 100 mg/kg and preferably from about 0.1 mg/kg to about 5 mg/kg.

A preferred oral dosage form, such as tablets or capsules, will contain the phosphorus-containing ACE inhibitor in an amount of from about 0.1 to about 500 mg, preferably from about 2 to about 5 mg, and more preferably from about 1 to about 3 mg.

For parenteral administration, the phosphorus-containing ACE inhibitor will be employed in an amount within the range of from about 0.005 mg/kg to about 10 mg/kg and preferably from about 0.005 mg/kg to about 0.3 mg/kg.

For oral administration, a satisfactory result may be obtained employing the HMG CoA reductase inhibitor in dosages employed, for example, for lovastatin as indicated in the Physician's Desk Reference, such as in an amount within the range of from about 1 to 2000 mg, and preferably from about 4 to about 200 mg. The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount of from about 0.1 to about 100 mg, preferably from about 5 to about 80 mg, and more preferably from about 10 to about 40 mg.

A preferred oral dosage form, such as tablets or capsules will contain the squalene synthetase inhibitor in an amount of from about 10 to about 500 mg, preferably from about 25 to about 200 mg.

The other serum cholesterol lowering drugs when present will be employed in dosages normally employed as indicated in the Physician's Desk Reference, for each of such agents such as in an amount within the range of from about 2 mg to about 7500 mg and preferably from about 2 mg to about 4000 mg.

The phosphorus-containing ACE inhibitor and cholesterol lowering agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

Tablets of various sizes can be prepared, e.g., of about 2 to 2000 mg in total weight, containing one or both of the active substances in the ranges described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonsful.

Such dosage forms can be administered to the patient on a regimen of one to four doses per day.

According to another modification, in order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

Fixed combinations of phosphorus-containing ACE inhibitor and cholesterol lowering drug are more convenient and are preferred, especially in tablet or capsule form for oral administration.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

Some of the active substances described above form commonly known, pharmaceutically acceptable salts such as alkali metal and other common basic salts or acid addition salts, etc. References to the base substances are therefore intended to include those common salts known to be substantially equivalent to the parent compound.

The formulations as described above will be administered for a prolonged period, that is, for as long as the potential for elevated cholesterol and atherosclerosis remains or the symptoms continue. Sustained release forms of such formulations which may provide such amounts biweekly, weekly, monthly and the like may also be employed. A dosing period of at least one to two weeks are required to achieve minimal benefit.

The following Examples represent preferred embodiments of the present invention.

EXAMPLES 1 AND 2

Fosinopril formulations suitable for oral administration for reducing serum cholesterol are prepared as described below.

1000 tablets each containing 10 mg fosinopril (Example 1) and 1000 tablets each containing 20 mg fosinopril (Example 2) are produced from the following ingredients.

| Fosinopril Sodium Tablets, 10 mg and 20 mg | | |
|---|---|---|
| Ingredient | Example 1 | Example 2 |
| Fosinopril Sodium, at 100% | 10.0 g | 20 g |
| Lactose NF anhydrous[1] | 138.0 g | 127.5 g |
| Microcrystalline Cellulose NF | 40 g | 40 g |
| Crospovidone NF | 7 g | 7 g |
| Providone USP | 4 g | 4 g |
| Magnesium stearate NF[2] | 1 g | 1.5 g |
| Alcohol SD#3A[3] | q.s. | q.s. |
| Total Weight | 200 g | 200 g |

[1]The amount of lactose will vary in accordance with the potency of the fosinopril sodium.
[2]The range for magnesium stearate is 0.3 to 1.5%.
[3]Alcohol SD#3A is used for granulating purposes and does not appear in the final product.

The fosinopril and lactose are admixed with the crospovidone and providone and alcohol. The mixture is dried and ground to a fine powder. The microcrystalline cellulose and magnesium stearate are admixed with the granulation. The mixture is compressed in a tablet press to form 1000 tablets each containing 10 mg fosinopril (Example 1) and 1000 tablets each containing 20 mg fosinopril (Example 2).

EXAMPLE 3

A fosinopril formulation suitable for oral administration for reducing serum cholesterol is prepared as described below.

1000 tablets each containing 15 mg of fosinopril are produced from the following ingredients.

| Fosinopril | 15 g |
|---|---|
| Corn starch | 50 g |
| Gelatin | 7.5 g |
| Avicel (microcrystalline cellulose) | 25 g |
| Magnesium stearate | 2.5 g |

The fosinopril and corn starch are admixed with an aqueous solution of the gelatin. The mixture is dried and ground to a fine powder. The Avicel and then the magnesium stearate are admixed with the granulation. This is then compressed in a tablet press to form 1000 tablets each containing 15 mg of active ingredient.

EXAMPLE 3A

A pravastatin formulation in the form of tablets having the following composition was prepared as described below.

| Ingredient | Parts by Weight |
|---|---|
| Pravastatin | 10 |
| Lactose | 67 |
| Microcrystalline cellulose | 20 |
| Croscarmellose sodium | 2 |
| Magnesium stearate | 1 |
| Magnesium oxide | 3 |

Pravastatin, magnesium oxide and a fraction (30%) of the lactose were mixed together for 2 to 10 minutes employing a suitable mixer. The resulting mixture was passed through a #12 to #40 mesh size screen. Microcrystalline cellulose, croscarmellose sodium and the remaining lactose were added and the mixture was mixed for 2 to 10 minutes. Thereafter, magnesium stearate was added and mixing was continued for 1 to 3 minutes.

The resulting homogeneous mixture was then compressed into tablets each containing 10 mg pravastatin which may be used in combination with fosinopril for lowering serum cholesterol.

The pravastatin tablets and fosinopril tablets may be administered as a combination in accordance with the teachings of the present invention to lower serum cholesterol. In addition, the pravastatin and fosinopril tablets may be ground up into powders and used together in a single capsule.

EXAMPLE 4

A ceronapril formulation suitable for oral administration in reducing serum cholesterol and inhibiting formation of fatty streak lesions is set out below.

1000 tablets each containing 100 mg of (S)-1-[6-amino-2-[[hydroxy(4-phenylbutyl)phosphinyloxy-1-oxohexyl]-L-proline were produced from the following ingredients.

| (S)-1-[6-Amino-2-[[hydroxy(4-phenyl-butyl)phosphinyl]oxy-1-oxohexyl]-L-proline (ceronapril, SQ29,852) | 100 g |
|---|---|
| Corn starch | 50 g |
| Gelatin | 7.5 g |
| Avicel (microcrystalline cellulose) | 25 g |
| Magnesium stearate | 2.5 g |

The ceronapril and corn starch are admixed with an aqueous solution of the gelatin. The mixture is dried and ground to a fine powder. The Avicel and then the magnesium stearate are admixed with the granulation. This is then compressed in a tablet press to form 1000 tablets each containing 100 mg of active ingredient which is used for reducing serum cholesterol.

EXAMPLE 5

By substituting 100 g of the ACE inhibitor (±)-1-[2-[[hydroxy(4-phenylbutyl)phosphinyl]oxy]-1-oxopropyl]-L-proline, dilithium salt for the ceronapril in Example 4, 1000 tablets each containing 100 mg of such ACE inhibitor are produced which is useful in reducing serum cholesterol.

Example 6

1000 tablets each containing 200 mg of ACE inhibitor are produced from the following ingredients:

| | |
|---|---|
| 1-[(S)-2-[[[(±)-1-(Benzoylamino)-3-phenylpropyl]phosphinyl]oxy]-1-oxopropyl]-L-proline, dilithium salt (ACE inhibitor) | 200 g |
| Lactose | 100 g |
| Avicel | 150 g |
| Corn starch | 50 g |
| Magnesium stearate | 5 g |

The ACE inhibitor, lactose and Avicel are admixed, then blended with the corn starch. Magnesium stearate is added. The dry mixture is compressed in a tablet press to form 1000 505 mg tablets each containing 200 mg of active ingredient. The tablets are coated with a solution of Methocel E 15 (methyl cellulose) including as a color a lake containing yellow #6. The resulting tablets are useful in reducing serum cholesterol.

Example 7

Two piece #1 gelatin capsules each containing 25 mg of fosinopril are filled with a mixture of the following ingredients:

| | |
|---|---|
| Fosinopril | 25 mg |
| Magnesium stearate | 7 mg |
| USP lactose | 193 mg. |

The resulting capsules are useful in reducing serum cholesterol.

EXAMPLES 8 AND 9

An injectable solution for use in inhibiting loss of cognitive functions is produced as follows:

| | |
|---|---|
| Fosinopril or ceronapril | 500 mg |
| Methyl paraben | 5 mg |
| Propyl paraben | 1 mg |
| Sodium chloride | 25 g |
| Water for injection qs. | 5 l. |

The fosinopril or ceronapril preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml of solution in a concentration of 100 mg of active ingredient per ml of solution for injection.

EXAMPLES 10

Tablets containing 500 mg clofibrate by itself or in combination with 5 mg fosinopril may be employed in separate dosage forms or combined in a single capsule form to lower serum cholesterol in accordance with the present invention.

EXAMPLES 11 TO 13

Ciprofibrate, bezafibrate, clinofibrate alone or in combination with ceronapril or fosinopril may also be prepared in a manner described hereinbefore in Examples 1 to 3 for use in lowering serum cholesterol.

EXAMPLE 14

The effect of fosinopril and captopril, was tested on blood pressure, plasma lipids and the formation of foam cells in the aortic arch of hyperlipidemic hamsters.

METHODS

Experimental Design

First a dose of 100 mg/kg of fosinopril was tested on the blood pressure of hamsters. Once it was confirmed that this amount of fosinopril decreased blood pressure acutely, a separate 3 week atherosclerosis study was commenced with the 100 mg/kg/day dose. This two-step procedure was repeated. Fosinopril and captopril both at 50 mg/kg were run side by side in an acute blood pressure study. It was followed by a 3 week atherosclerosis experiment where 50 mg/kg/day of fosinopril and 50 mg/kg/day of captopril were compared.

Acute effects of fosinopril and captopril on blood pressure

Three groups of hamsters had their mean arterial pressure monitored once at 6, 17 or 25 hours respectively, after gavaging 100 mg/kg of fosinopril. These measurements were compared to a control group. Treated hamsters were fasted for 2 hours, then gavaged with drug and refed 2 hours after dosing. To measure mean arterial pressure, hamsters were anesthetized with methoxyfluorane and a catheter was inserted into the carotid artery. Mean arterial pressure and heart rate was continuously monitored on a polygraph. The nose cone containing anesthetic was removed and the hamster gradually regained consciousness; when the hind leg first twitched following a gentle pinching of the foot, mean arterial pressure and heart rate were recorded. The hamster was re-anesthetized and this procedure was repeated twice more to give an average of mean arterial pressure and heart rate for each animal in a semiconscious state.

In a separate study, two groups of hamsters were gavaged with 50 mg/kg of fosinopril and their mean arterial pressures were monitored once at either 6 or 17 hours. Another two groups treated with 50 mg/kg of captopril were measured at the same time points, and the four sets of hamsters were compared to a control group.

The effect of fosinopril and captopril on early atherosclerosis

In the first study, a group of controls were fed regular chow supplemented with 0.05% cholesterol, 10% coconut oil, 10% fiber and 15% rice flour. The controls were gavaged daily with water. A second group received the same atherogenic diet and was gavaged once daily with 100 mg/kg of fosinopril. Hamsters were fasted 2 hours before dosing, and refed 2 hours following gavage. A third group of hamsters was fed chow to provided base-line values for plasma lipids, blood pressure and atherosclerosis.

For the second study, a group of control hamsters was fed the same atherogenic diet as above. A second and third group received the atherogenic diet and were gavaged daily with 50 mg/kg fosinopril and 50 mg/kg captopril respectively. Each animal was weighed daily for accurate dosing and the weight change between the start and the end of the study was assessed.

In both atherosclerosis studies, hamsters were treated for 3 weeks. On day 19, animals were fasted overnight and bled the next morning to measure plasma lipids. At day 21, non-fasted hamsters had their mean arterial pressure and heart rate determined in a semiconscious state at 5 hours after gavaging. Then blood was collected into heparinized tubes to assay plasma levels of drug. The aortic arch was fixed by pressure-perfusion and the extent of fatty streak formation was measured in en face specimens. The arch was stained with hematoxylin and oil red 0 (for neutral lipid), cut open and mounted on a glass slide with the endothelial surface face up. Monocytes attached to the endothelial surface and macrophage/foam cells on the surface and in the subendothelial space (i.e. intimal cells) were counted and divided by the area of tissue giving foam cells/mm$^2$. In addition the average size of foam cells ($\mu$m$^2$) in each specimen was determined, and foam cell number multiplied by foam cell size ($\mu$m$^2 \times 10^3$) was used to approximate the area of artery stained by oil red 0.

In acute and chronic experiments, mean arterial pressure, heart rate, plasma lipids and atherosclerosis were analyzed by a Welch Trend test. This statistic tests for equality of group means versus a difference in the means (either increasing or decreasing). It assumes the data are normally distributed but it does not require equal within group variances. The level of significance was modified by the Bonferroni's method, depending on the number of comparisons made between control and treated groups. Thus the new levels of statistical significance were $P<0.017$ for Table 1 (i.e. 0.05 divided by 3), and $P<0.025$ for Table 2 to 6 (i.e. 0.05 divided by 2). A paired t test was used to compare changes in body weight within control and treated hamsters of the second lesion study.

RESULTS

Acute effects of fosinopril and captopril on blood pressure

Compared to controls, hamsters that were gavaged with 100 mg/kg of fosinopril had significant reductions in normal mean blood pressure of 19% and 10% at 6 and 17 hours respectively. By 25 hours blood pressure of the treated group was similar to controls and heart rate was not affected by fosinopril (Table 1). The 50 mg/kg dose of fosinopril and captopril decreased mean arterial pressure by 15% and 10% respectively at 6 hours. However the reduction with captopril just missed statistical significance ($P<0.04$). Values were normal in the two 17 hour groups. Heart rate was unchanged with fosinopril treatment, whereas the 6 hour captopril group had an 8% increase in heart rate compared to controls (Table 2).

The effects of fosinopril and captopril on early atherosclerosis

After three weeks of treatment, fosinopril (100 mg/kg/day) decreased arterial pressure by 11% compared to the control group. Heart rate was unchanged. Baseline hamsters had normal blood pressure and heart rate (Table 3). Compared to controls, fosinopril decreased plasma VLDL+LDL cholesterols and total triglycerides by 39% and HDL cholesterol increased by 18%. The baseline group had significantly lower plasma lipids than the control group. When the fosinopril group was compared to the baseline animals, the latter had lower total, VLDL+LDL cholesterols and total triglycerides of 28%, 30%, and 48% respectively (Table 3). As for the measurements of early atherosclerosis, both fosinopril and the baseline groups had 92% fewer foam cells/mm$^2$, the foam cells were 40% smaller and total foam cell area was 95% less when compared to the control group (Table 4).

In the second lesion study, the 50 mg/kg/day fosinopril and captopril groups had blood pressures and heart rates that were similar to controls (Table 5). Compared to the control group, fosinopril decreased plasma total, VLDL+LDL cholesterols and total triglycerides by 17%, 27% and 45% respectively. The captopril group had similar plasma lipid levels as the controls, except for HDL cholesterol which was 20% lower (Table 5). At the level of the arterial wall, fosinopril reduced the number of foam cells/mm$^2$, foam cell size and total foam cell area by 85%, 35% and 90% respectively, when compared to controls. Captopril treated hamsters had 44% fewer foam cells, and total foam cell area was 53% less compared to the control group (Table 6). Foam cell size was 16% smaller in captopril hamsters but the difference just missed significance ($P<0.032$). During this study, both control and fosinopril groups had significant increases in body weight of 8% and 3% respectively. The captopril treated hamsters had no change in body weight (Table 7).

DISCUSSION

This series of experiments indicate that fosinopril and captopril inhibited the formation of the fatty streak in the hyperlipidemic hamster. There are several possible mechanisms behind fosinopril's anti-atherosclerotic effect. With both fosinopril doses, the decline of VLDL+LDL cholesterols probably contributed since in a previous hamster study, the hypolipidemic drug cholestyramine decreased the same fraction of cholesterol and also reduced early atherosclerosis. The increase in HDL cholesterol with the high fosinopril dose may have also affected lesion formation, as HDL$_2$ is the predominant fraction in hamsters, which removes cholesterol from tissues. Whether a decrease in the level of plasma triglycerides played a role remains unclear.

The data suggest that the decline of VLDL+LDL cholesterols with fosinopril treatment cannot entirely explain the decrease in foam cell formation. For example, the captopril group had similar levels of plasma lipids compared to controls, while the extent of the lesions was less. In addition, fosinopril at 100 mg/kg inhibited the fatty streak to the same extent as in the baseline hamsters, despite having higher VLDL+LDL cholesterols. Finally, fosinopril at 50 mg/kg decreased atherosclerosis to a greater degree than drugs such as cholestyramine, which only lower plasma cholesterol.

The mechanism whereby fosinopril decreases plasma VLDL+LDL cholesterols is uncertain. Body weights of the 50 mg/kg fosinopril group increased during the study. The captopril treated animals failed to gain weight but they achieved similar plasma lipid levels as the controls. Both results indicate that reduced levels of plasma cholesterol in the fosinopril group cannot be explained by a low intake of dietary cholesterol and saturated fat.

The reduction of mean arterial pressure with fosinopril treatment may have inhibited foam cell formation. However there are several reasons why this may not be the case. For example, the 50 mg/kg/day dose of fosinopril only temporarily reduced blood pressure and yet it dramatically inhibited foam cell formation. In fact the same dose of captopril failed to significantly decrease pressure in both acute and chronic studies, and still it produced a decline of the fatty streak. The data suggests that both fosinopril and captopril slowed the progression of early atherosclerosis by additional mechanism(s) beyond decreases in plasma cholesterol or blood pressure.

To conclude, fosinopril decreased the progression of the fatty streak probably through a reduction of plasma VLDL+LDL cholesterols and a temporary fall in blood pressure. Captopril inhibited foam cell accumulation without affecting blood pressure or plasma lipids. The data suggests that phosphorus-containing ACE inhibitors such as fosinopril possibly impede early atherosclerosis by additional mechanism(s) such as decreasing the concentration of arterial angiotensin II.

SUMMARY

The effect of fosinopril and captopril on the development of the fatty streak was determined in hyperlipidemic hamsters. Early atherosclerosis was induced by feeding chow containing 0.05% cholesterol and 10% coconut oil. Acute dose-blood pressure response studies in hamsters, indicated that fosinopril (100 and 50 mg/kg/day) decreased mean arterial pressure by 19% and 15% respectively at 6 hours after gavage. Captopril (50 mg/kg/day) reduced mean arterial pressure at 6 hours by 10%, but this just missed statistical significance. In the atherosclerosis experiments, three weeks of treatment with 100 mg/kg/day of fosinopril decreased blood pressure by 11%. Chronic dosing with the 50 mg/kg dose of either fosinopril or captopril had no effect on blood pressure. Compared to controls, fosinopril (100 and 50 mg/kg/day) reduced plasma VLDL+LDL cholesterols by 39% and 27% respectively, while the high dose of fosinopril increased HDL cholesterol by 18%. Total triglycerides were reduced by approximately 40% with both doses of fosinopril. Captopril treatment had no effect on plasma lipids. Measurements of early atherosclerosis demonstrated that fosinopril (100 mg/kg/day) reduced the number of intimal foam cells/mm², foam cell size (μm²) and total foam cell area (μm²) by 92%, 40% and 95% respectively. The lower dose of fosinopril decreased the three fatty streak parameters by 85%, 38% and 90% respectively. Captopril reduced these measurements by 44%, 16% and 53%. In conclusion, fosinopril lowered blood pressure acutely, decreased plasma cholesterol and inhibited fatty streak formation. Captopril reduced the fatty streak without affecting plasma lipids or blood pressure.

TABLE 1

Effects of Fosinopril 100 mg/kg p.o. on Mean Arterial Pressure (MAP) and Heart Rate (HR) in Normotensive Hamsters

| | Control Group | Hours after gavaging 100 mg/kg of Fosinopril | | |
|---|---|---|---|---|
| | | 6 Hour Group | 17 Hour Group | 25 Hour Group |
| MAP mm Hg | 135 ± 3 | 109 ± 4[a] | 121 ± 3[a] | 133 ± 8 |
| HR beats/min. | 367 ± 8 | 392 ± 5 | 360 ± 4 | 393 ± 9 |
| n | 7 | 8 | 6 | 4 |

Values are mean ± SEM
[a] $P < 0.017$ compared to the control group (Welch trend test).

TABLE 2

Effects of Fosinopril and Captopril 50 mg/kg p.o. on Mean Arterial Pressure and Heart Rate in Normotensive Hamsters

| | Control Group | Hours after gavaging 50 mg/kg of drug | | | |
|---|---|---|---|---|---|
| | | Fosinopril | | Captopril | |
| | | 6 Hour Group | 17 Hour Group | 6 Hour Group | 17 Hour Group |
| MAP mm Hg | 136 ± 3 | 116 ± 4[a] | 133 ± 4 | 123 ± 5 | 136 ± 3 |
| HR beats/min. | 368 ± 6 | 369 ± 6 | 371 ± 6 | 398 ± 6[a] | 351 ± 6 |
| n | 10 | 7 | 8 | 8 | 7 |

Values are mean ± SEM
[a] $P < 0.025$ compared to control group (Welch trend test)

TABLE 3

Mean Arterial Pressure, Heart Rate and Plasma Lipids of Control, Fosinopril Treated and Baseline Hamsters

| | MAP mm Hg | HR beats/min. | TC mg/dl | VLDL + LDL-C mg/dl | HDL-C mg/dl | TG mg/dl | n |
|---|---|---|---|---|---|---|---|
| Control | 133 ± 2 | 346 ± 6 | 192 ± 17 | 132 ± 17 | 60 ± 2 | 417 ± 55 | 14 |
| Fosinopril 100 mg/kg | 118 ± 2[a] | 350 ± 4 | 151 ± 10 | 81 ± 9[a] | 71 ± 2[a] | 254 ± 18[a] | 14 |
| Baseline | 130 ± 3 | 333 ± 5 | 109 ± 4[a] | 57 ± 3[a] | 52 ± 3[a] | 132 ± 19[a] | 15 |

Values are mean ± SEM
[a] $P < 0.025$ compared to the control group (Welch Trend test).
TC: total cholesterol
HDL-C: HDL cholesterol
VLDL + LDL-C: VLDL + LDL cholesterol
TG: total triglycerides

TABLE 4

Fatty Streak Formation in Control, Fosinopril Treated and Baseline Hamsters

| | Adherent Monocytes per mm² | Intimal Foam Cell per mm² | Foam Cell Size μm² | Total Foam Cell Area μm² × 10³ | n |
|---|---|---|---|---|---|
| Control | 3.2 ± 0.3 | 53 ± 11 | 106 ± 8 | 82 ± 20 | 10 |
| Fosinopril 100 mg/kg | 2.7 ± 0.3 | 4 ± 1[a] | 63 ± 2[a] | 4 ± 1[a] | 10 |
| Baseline | 3.0 ± 0.3 | 4 ± 2[a] | 64 ± 4[a] | 4 ± 2[a] | 8–13 |

Values are mean ± SEM
[a] $P < 0.025$ compared to the control group (Welch Trend test).

TABLE 5

Mean Arterial Pressure, Heart Rate and Plasma Lipids of Control, Fosinopril and Captopril Treated Hamsters

| | MAP mm Hg | HR beats/min. | TC mg/dl | VLDL + LDL-C mg/dl | HDL-C mg/dl | TG mg/dl | n |
|---|---|---|---|---|---|---|---|
| Control | 136 ± 2 | 354 ± 15 | 236 ± 9 | 161 ± 9 | 75 ± 2 | 428 ± 27 | 12 |
| Fosinopril 50 mg/kg | 136 ± 2 | 360 ± 6 | 195 ± 9$^a$ | 118 ± 7$^a$ | 77 ± 3 | 237 ± 10$^a$ | 12 |
| Captopril 50 mg/kg | 135 ± 2 | 351 ± 6 | 246 ± 11 | 186 ± 11 | 60 ± 2$^a$ | 469 ± 26 | 12 |

Values are mean ± SEM
$^a$P <0.025 compared to the control group (Welch Trend test).
TC: total cholesterol
HDL-C: HDL cholesterol
VLDL + LDL-C: VLDL + LDL cholesterol
TG: total triglycerides

TABLE 6

Fatty Streak Formation in Control, Fosinopril and Captopril Treated Hamsters

| | Adherent Monocytes per mm$^2$ | Intimal Foam Cells per mm$^2$ | Foam Cell Size μm$^2$ | Total Foam Cell Area μm$^2$ × 10$^3$ | n |
|---|---|---|---|---|---|
| Control | 3.5 ± 0.2 | 72 ± 10 | 109 ± 3 | 113 ± 18 | 12 |
| Fosinopril 50 mg/kg | 3.5 ± 0.4 | 11 ± 2$^a$ | 68 ± 4$^a$ | 11 ± 3$^a$ | 11 |
| Captopril 50 mg/kg | 2.8 ± 0.3 | 40 ± 8$^a$ | 92 ± 8 | 53 ± 14$^a$ | 12 |

Values are mean ± SEM
$^a$P <0.025 compared to the control group (Welch Trend test).

TABLE 7

Body weights in grams of Control and Experimental Hamsters at the Start and at the End of the Study

| | Control | Fosinopril 50 mg/kg | Captopril 50 mg/kg |
|---|---|---|---|
| Start | 119 ± 2 | 115 ± 2 | 120 ± 3 |
| End | 129 ± 2$^a$ | 119 ± 2$^a$ | 121 ± 3 |

Values are mean ± SEM
$^a$P <0.001 compared to body wieght at the start of the study (paired t test).

What is claimed is:

1. A method for lowering serum cholesterol in a mammalian species, which comprises administering to a patient in need of treatment a therapeutically effective amount of a phosphorus-containing angiotensin converting enzyme inhibitor.

2. The method as defined in claim 1 wherein the phosphorus-containing angiotensin converting enzyme inhibitor is a phosphinylalkanoyl proline, a phosphinylalkanoyl substituted proline, a phosphonamidate derivative or a phosphonate substituted amino or imino acid or salt thereof.

3. The method as defined in claim 1 wherein the phosphorus-containing angiotensin converting enzyme inhibitor is fosinopril.

4. The method as defined in claim 1 wherein the phosphorus-containing angiotensin converting enzyme inhibitor is ceronapril.

5. The method as defined in claim 1 wherein the phosphorus-containing angiotensin converting enzyme inhibitor is a phosphinylalkanoyl proline or substituted proline.

6. The method as defined in claim 1 wherein said phosphorus-containing angiotensin converting enzyme inhibitor is administered in single or divided doses of from about 0.1 to about 500 mg/one to four times daily.

7. The method as defined in claim 1 wherein the phosphorus-containing angiotensin converting enzyme inhibitor is administered to a hypertensive patient.

8. The method as defined in claim 1 wherein the phosphorus-containing angiotensin converting enzyme inhibitor is administered to a normotensive patient.

* * * * *